United States Patent [19]
Peyman

[11] Patent Number: 6,162,242
[45] Date of Patent: Dec. 19, 2000

[54] SELECTIVE PHOTODYNAMIC TREATMENT

[76] Inventor: Gholam A. Peyman, 8654 Pontchartrain Blvd., Apartment 1, New Orleans, La. 70124

[21] Appl. No.: 09/235,104

[22] Filed: Jan. 21, 1999

[51] Int. Cl.⁷ .............................. A61N 5/01; A61B 19/00
[52] U.S. Cl. .............................................. 607/88; 128/898
[58] Field of Search ................................ 128/898; 606/2, 606/4; 607/88, 89; 604/20

[56] References Cited

U.S. PATENT DOCUMENTS

| | | | |
|---|---|---|---|
| 5,707,986 | 1/1998 | Miller et al. | 514/185 |
| 5,798,349 | 8/1998 | Levy et al. | 514/185 |

OTHER PUBLICATIONS

Peng et al., *5–Aminolevulinic Acid–Based Photodynamic Therapy*, Cancer, 79, No. 12 (Jun. 1997).

Webber et al., *On–line fluorescence of human tissues after oral administration of 5–aminolevulinic acid*, Journal of Photochemistry and Photobiology B:Biology 38, pp. 209–214 (1997).

Rick et al., *Pharmacokinetics of 5–aminolevulinic acid–induced protoporphyrin IX in skin and blood*, Journal of Photochemistry and Photobiology B:Biology 40, pp. 313–319 (1997).

Peyman et al., *Photodynamic Therapy for Choriocapillaris Using Tin Ethyl Etiopurpurin (SnET2*, Ophthalmic Surgery and Lasers, 28, No. 5, pp. 409–417 (May 1997).

Makinen, et al., *Protoporphyrin–IX Distribution and Photodynamic Effect in Rat Oesophagus after Aminolaevulinic Acid Administration*, Scand. J. Gastroenterol. 32, pp. 633–637 (1997).

Charlesworth and Truscott, *The use of 5–aminolevulinic acid (ALA) in photodynamic therapy (PDT)*, News and Views.

*Primary Examiner*—Linda C. M. Dvorak
*Assistant Examiner*—Jocelyn Debra Ram
*Attorney, Agent, or Firm*—Wood, Herron & Evans, L.L.P.

[57] ABSTRACT

A method and apparatus for selectively targeting photodynamic therapy (PDT) to abnormal tissues. The abnormal tissues may be neovascular intraocular tissue or neoplastic cells. In the eye, a photosensitizing agent is to the vessels then the vessels are collapsed by application of pressure before PDT. Abnormal vessels allow agent to leak into the surrounding tissues, while agent in normal vessels is contained. Upon pressure-induced collapse of intraocular vessels, agent is removed from the vessels and is targeted by subsequent PDT only in surrounding tissues which are susceptible to PDT. Vessel occlusion may be enhanced by administering agents to promote and/or prevent dissolution of clots. The interaction of light with the photosensitizing agent which leaked from neovascular tissue results in cellular or tissue destruction in areas where the agent is located. Thus, normal vessels have no photosensitizing agent and are undamaged by light radiation, while abnormal areas are treated. An apparatus to regulate intraocular pressure is also disclosed.

18 Claims, 3 Drawing Sheets

SELECTIVE PHOTODYNAMIC TREATMENT

FIELD OF THE INVENTION

This invention relates to a device and method to selectively treat abnormal cells, particularly abnormal blood vessels, using a photosensitizing agent susceptible to photodynamic therapy.

BACKGROUND OF THE INVENTION

Many therapeutic treatments of pathological conditions involve selective targeting of specific tissues or cells for destruction. For example, a goal in cancer therapy is to destroy only malignant cells while leaving normal cells undisturbed. As another example, a goal in ophthalmology is to destroy new blood vessels in the eye that can result in visual impairment if allowed to proliferate, while leaving normal existing blood vessels intact.

In the mammalian eye, macular degeneration is a pathological condition that results in proliferation of new blood vessels in the subretinal area. The new blood vessels proliferate from the choriocapillaris through defects in Bruch's membrane beneath or on top of retinal pigment epithelium (RPE), and form vascular membranes. While the presence of the new vessels themselves is not problematic, new vessels leak blood and other serous fluid which accumulate in surrounding spaces. It is this fluid accumulation that leads to visual impairment. For example, the accumulation of fluid can result in serous and hemorrhagic detachment of the RPE and neurosensory retina, and can lead to loss of vision due to fibrous deform scarring. Therefore, methods to prevent or control the growth of subretinal new blood vessels and/or to alter their "leakiness" have been devised to protect retinal integrity.

In the retina, both the large vessels and the capillaries normally have intact vessel walls. In the choroid, the large vessels normally have intact vessel walls but the capillary walls or membranes contain fenestrations or openings. Any endogenous or exogenous fluid present in these capillaries, for example, blood, serous fluid, solubilized drug, etc. will leak outside the vessels and into the surrounding area. An example of an exogenously administered drug is a photosensitizing drug that is administered to an individual for subsequent phototreatment with photodynamic therapy (PDT). PDT is a method for local and selective tissue or cellular destruction by the action of a particular wavelength of light on the photosensitizing drug. The wavelength of light is selected to correspond to the absorbance spectrum of the photosensitizing agent.

In normal vessels with intact membranes, an intravenously administered compound such as a photosensitizing agent is confined to the vessel lumen. The surrounding tissue, since it contains little if any photosensitizing agent, is not damaged by subsequent laser treatment. In addition, cytotoxic oxygen species such as hydroxyl or oxygen free radicals produced at the irradiation site have short diffusion distances and are similarly locally confined. Also, the low energy levels of the laser treatment in PDT spare normal adjacent tissues. Since there is no thermal damage, and since nonthermal light activation leads to only localized, selective photochemical thrombosis, PDT is selective for a specific area.

PDT ideally occurs when tissue levels of the photosensitizing agent are at a maximum. Neovascular tissue, like the normal choriocapillaries, have fenestrations in the vessel wall which allow some portion of the administered photosensitizing drug to escape from the lumen and into the surrounding tissue spaces. The leakage and pooling of fluid permits photosensitizing agent administered into a vessel to be located in both the vessel lumen and outside the vessel, leading to generalized tissue destruction in the area containing the photosensitizing agent.

One method to control fluid leakage from choroidal and new subretinal vessels is laser photocoagulation using lateral transfer of heat. Laser photocoagulation uses a cautery-like method to coagulate fluid escaping from the vessel wall. However, while it is effective to control fluid leakage in some patients, it is not entirely satisfactory. For example, it seldom confines the extent of damage to choroidal neovascular tissue, since there is heat-generated destruction of unaffected areas of the retina, including the neurosensory retina and RPE overlying the vascular leakage sites. Laser photocoagulation thus lacks the desired specificity to target only new blood vessels. Additionally, there is a persistent or recurrent choroidal neovascularization following repeated laser photocoagulation that frequently leads to more severe visual loss over time.

Another method to control fluid leakage from choroidal and subretinal vessels is PDT. PDT is more protective of normal tissue than laser photocoagulation because there is no heat applied so laser treatment may be localized to a specific area. PDT has gained wide clinical acceptance as a mechanism for producing localized, selective photochemical thrombosis. For example, PDT has been suggested as being able to play an important adjuvant role in treatment of cancers of the gastrointestinal tract and has been used to treat cancers of the esophagus, duodenum and colon. A photosensitizer prodrug, preferably aminolevulinic acid (ALA), is orally administered and is absorbed by the gastrointestinal tract. ALA is metabolized in vivo to protoporphyrin, the active photosensitizing agent. Protoporphyrin preferentially accumulates in the cytoplasm of neoplastic, versus normal, cells. A drawback of this treatment is that the oral route of administration of the agent leads to a weaker photosensitizing response than other routes of administration, e.g. intravenous administration.

Unfortunately, the results of PDT in ophthalmologic treatment have not been as promising; PDT is too nonspecific in that normal retinal vessels are damaged along with subretinal vessels. Also, there are unresolved issues with PDT such as the time interval between drug administration and light application, and the selective targeting of abnormal vessels with drug, light, or both.

Current methods in treating macular degeneration, such as laser photocoagulation, do not confine treatment to only new abnormal vessels. Thus, normal healthy blood vessels are destroyed, causing a decreased intraocular blood flow. In addition, laser treatment must continually be repeated as new vascularizations occur. Current methods in treating cancer are beginning to recognize the need to control the vascular supply to neoplastic cells.

Simply put, control of blood vessels is a way to treat certain pathological conditions such as macular degeneration and cancer. Macular degeneration results in new, inherently "leaky", blood vessels in the eye. These new leaky vessels allow fluid to escape and pool in the surrounding tissues. The accumulation of fluid results in scar formation which can damage the eye and lead to altered vision. In cancer, it is recognized that new blood vessels play a role in nourishing malignant cells. A goal in the treatment of both diseases is to destroy the new abnormal blood vessels but leave normal blood vessels undisturbed.

Thus, there remains a need for a therapeutic method to effectively target undesired and/or abnormal vessels while leaving normal vessels intact.

SUMMARY OF THE INVENTION

The invention is directed to a method to selectively phototreat an abnormal intraocular blood vessel, using a photosensitizing agent that is susceptible to photodynamic therapy (PDT), without affecting normal intraocular blood vessels. A photosensitizing agent susceptible to phototreatment is administered into both normal and abnormal vessels, the abnormal vessels having an altered membrane that allows the agent to be released from the vessel through its altered membrane and into a site adjacent the abnormal vessel, while being maintained within the normal vessel. After a sufficient time for the agent in the vessel to be released into the adjacent site, both the normal and abnormal vessels are transiently constricted. This allows the agent to be substantially displaced from the normal vessels at a treatment site, thereby preserving their viability during phototreatment. In addition, the transient nature of the constriction preserves intraocular structures that are nourished by the constricted blood vessels. The site is then treated with photodynamic therapy (PDT), that is, it is phototreated for a defined time. The selective location of agent in the area adjacent abnormal vessels, with substantially no agent in the area adjacent normal vessels, selectively treats abnormal vessels. The normal and abnormal vessels are then restored to their unconstricted state.

The invention also includes enhancing vascular occlusion by administering a vessel occluding agent. The agent may work by enhancing thrombus formation and/or preventing thrombus dissolution. For example, adenosine diphosphate (ADP) may be administered at a dose of about 50 $\mu$g/kg to about 10 mg/kg to enhance thrombus formation, and $\epsilon$-aminocaproic acid, tranexamic acid or aprotinin may be administered to prevent thrombus dissolution. These agents may be administered either prior to, during or subsequent to PDT.

The invention is also directed to an apparatus for regulating intraocular pressure. The apparatus comprises a contact lens and may have an inflatable tube surrounding at least a portion of the lens and connected to a pressure source.

The invention is still further directed to a method to selectively treat an abnormal cell and blood vessel adjacent the abnormal cell by using a photosensitizing agent susceptible to a phototreatment. The agent is administered into the blood vessel and to the abnormal cell, then the vessel and cell are phototreated. A vessel occluding agent to enhance vascular occlusion may also be used.

The invention is additionally directed to a method to enhance phototreatment of a malignant cell supplied by a blood vessel by administering a photosensitizing agent. A vessel occluding agent to enhance vascular occlusion may also be used. The photosensitizing agent is administered to the vessel and the malignant cell, then the vessel and malignant cell are thereafter phototreated.

These and other embodiments of the invention will be further described in the following figures, detailed description and example.

DETAILED DESCRIPTION

Phototreatment or photodynamic therapy (PDT) is used to selectively target a desired area of the body for treatment. A photosensitive agent or drug is administered, then after a certain time period a light source with a wavelength corresponding to the absorbance spectrum of the administered agent is targeted to the particular site for treatment. A laser is preferably used to direct the light to only the specific tissue or area to be treated. The time period between administration of the agent and phototreatment is usually between about 1–60 min. The agent, upon activation by the defined wavelength of light, produces cytotoxic oxygen radicals. These radicals disrupt microvascular structures in the treatment area and result in subsequent tissue damage. The extent of the damage may vary, but may include death of some or all of the cells that comprise the tissue. Thus, treatment may range from cell injury to cell death.

Phototreatment has a dual beneficial effect in treatment of neoplastic cells. It provides a selective coagulation in site-specific areas, thus depleting malignant cells of nourishment by depleting their blood supply. Additionally, the free radicals formed in phototreatment directly injure cells by disrupting normal cellular processes and thus provide an additional mechanism of cellular injury or death. Since the cytotoxic effect is localized due to the short half-life of the radicals, malignant cells are selectively destroyed over normal cells.

Figure 1:
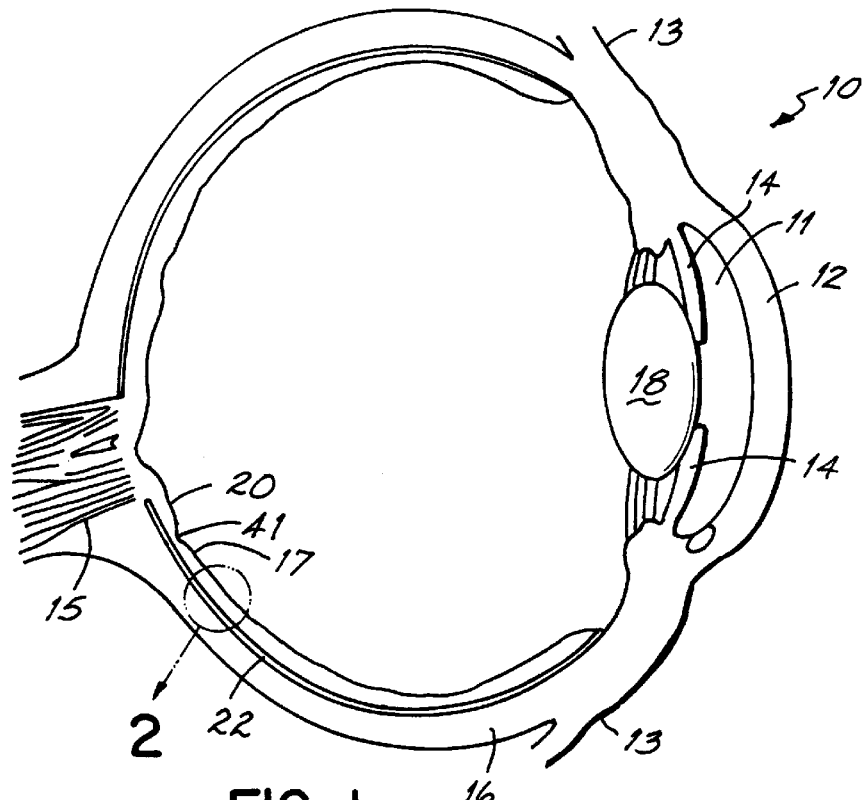
FIG. 1 is a schematic cross-sectional view of a mammalian eye.

With reference to FIG. 1, a mammalian eye 10 is shown. The locations of the anterior chamber 11, cornea 12, conjunctiva 13, iris 14, optic nerve 15, sclera 16, macula lutea 17, lens 18, retina 20 and choroid 22 are illustrated.

Figure 2:
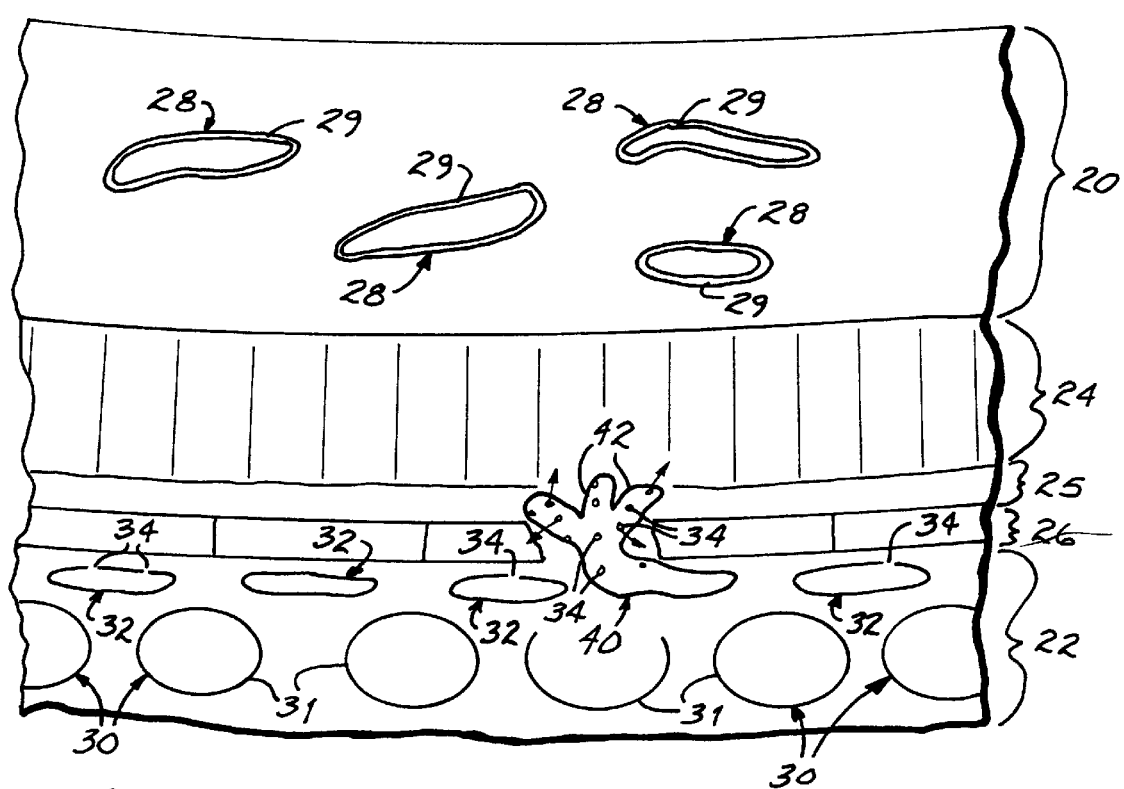
FIG. 2 is an enlarged diagrammatic illustration of the circled area 2 of FIG. 1 showing detailed retinal and choroid structures.

FIG. 2 is a diagrammatic enlargement of the circled area of FIG. 1. Between the retina 20 and the choroid 22 there is an outer segment of photoreceptor cells 24 including rods and cones, a subretinal space 25, and a layer of retinal pigment epithelium (RPE) 26. In a normal adult, retinal blood vessels 28, including capillaries, have walls or membranes 29 that contain no fenestrations or openings. In a normal adult, the large choroidal vessels 30 similarly have walls 31 that contain no fenestrations but the choriocapillaries 32 have walls that contain fenestrations 34. In an adult with macular degeneration, there is growth of new subretinal blood vessels whose walls or membranes are altered in that they also contain fenestrations.

Macular degeneration is a pathological, progressive age-related degeneration in the macula lutea 17 of the retina 20. The macula lutea 17 is located in the center of the posterior part of the retina 20 and is the most sensitive portion of the retina 20. In the center of the macula lutea 17 is a depression, the fovea centralis 41, from which rods are absent. About one-tenth inch inside the fovea 41 is the point of entrance of the optic nerve 15 and its central artery. At this point, the retina 20 is incomplete and forms the blind spot.

In macular degeneration, subretinal neovascular tissue 40 develops in the choroid 22. The neovascular tissue 40 penetrates the RPE and subretinal space 25, and extends into the area containing photoreceptor cells 24. The neovascular tissue 40 has membranes or walls 42 that are altered in having fenestrations 34, that permit fluid leakage into spaces surrounding photoreceptor cells 24, the subretinal space 25 and the RPE 26.

Neovascular tissue 40 results in visual impairment because of fluid leakage and accumulation in surrounding spaces. Treatment of macular degeneration results in destruction of the neovascular tissue 40. Treatment consists of sensitizing the tissue 40 to light by administration of a photosensitizing agent, then exposing the sensitized tissue to light of one or more defined wavelengths. The selection of PDT agents depends upon several factors such as sites of tissue distribution requiring treatment, the mechanisms of action of the agents themselves, and their specific optimal absorption wavelengths. For example, tin ethyl etiopurpurin (SnET2), also used in phase III studies of cutaneous cancers and AIDS related Kaposi's sarcoma, is frequently used as a PDT agent. SnET2 has several advantages, such as lower persistence and severity of skin photosensitivity, absorption at longer wavelengths yielding better tissue penetration, a higher extinction coefficient resulting in increased potency and efficiency, ease of synthesis and ability to be produced in a highly pure form.

As another example, protoporphyrin is a good photosensitizing agent. Protoporphyrin IX is a photoactive compound which is endogenously formed from 5-aminolevulinic acid (ALA) in the biosynthetic pathway of heme. ALA may be applied topically and is metabolized to protoporphyrin, the active photosensitizing agent. Laser irradiation is usually at a wavelength in the range of about 630 nm, or alternatively in the range of 670 nm. ALA administration is particularly useful in PDT for cancer treatment, since ALA-induced protoporphyrin accumulation is greater in certain malignant cells. ALA may be administered orally in a bolus as an aqueous solution at a concentration of about 60 mg/kg body weight, or intravenously at a concentration of 30 mg/kg body weight. Other photosensitizing agents that may be used include benzoporphyrin derivative monoacid tube A(BPD-MA) and mono-l-aspartyl chlorine 6 (NPe6), with absorbance maxima in the range of about 660–690 nm. Progesterone (Lutex) may also be used. The extent of SnET2-induced damage to the RPE depends upon the dose of light administered. Photodamage, unlike the diffuse damage caused by laser photocoagulation, is confined to only the tissues containing the photosensitizing agent. In addition, photodamage is less than that produced by laser photocoagulation since the photosensitizer is confined primarily to the vasculature in normal tissues, and the RPE is the main absorber of light energy in laser photocoagulation. The RPE over a site treated with PDT recovers within two to four weeks of treatment. Finally, there is no apparent systemic toxicity when SnET2 is administered in 0.5 and 1 mg/kg doses, and clinical studies indicate that there is a significant margin of safety.

The photosensitizing agent is administered into the vessels, preferably by intravenous injection, and is transported in the blood to vessels 28 in the retina 20. The retinal capillaries 28, having intact walls 29 with no fenestrations, retain the photosensitizing agent within their lumen. In contrast, the subretinal choriocapillaries 32, having fenestrations 34 in their walls, cannot retain the photosensitizing agent within the lumen of the vessel 32 and the photosensitizing agent leaks into the surrounding space. Thus, the tissue adjacent neovascular tissue 40 contains the photosensitizing agent. Tissue adjacent normal vessels contain essentially no photosensitizing agent.

Figure 3:
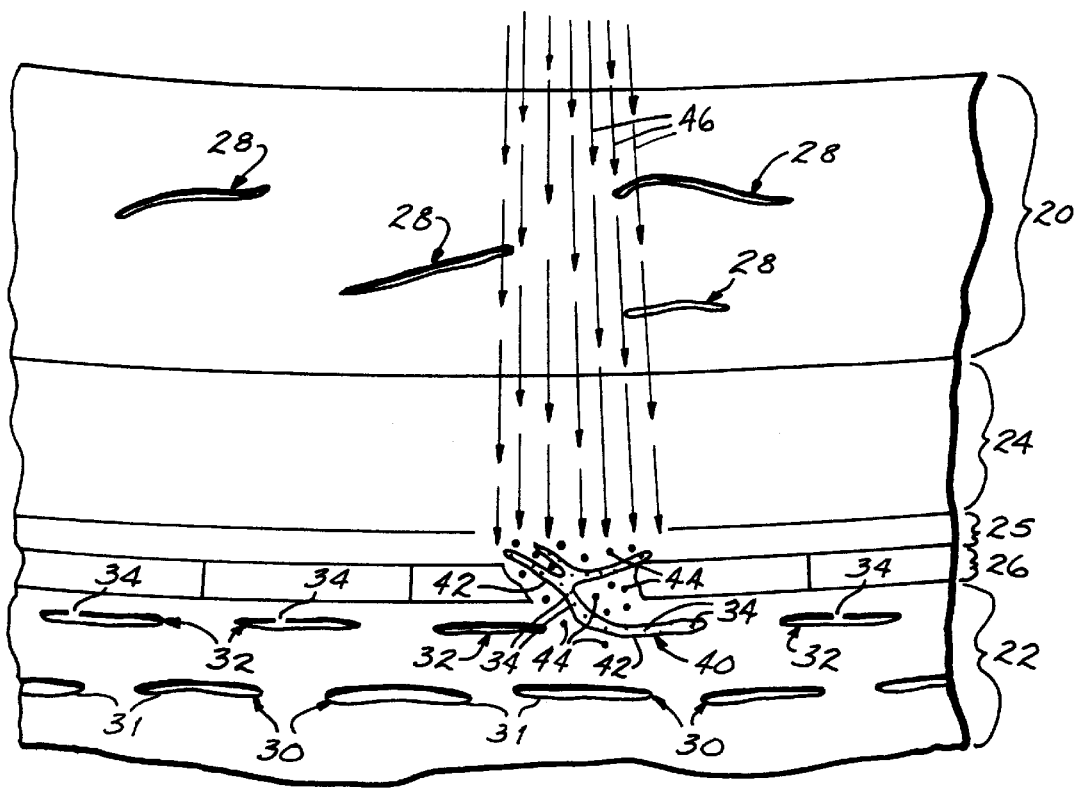
FIG. 3 is a diagrammatic illustration of the choroid and retina of FIG. 2 treated using the method of the invention.

With reference to FIG. 3 the normal vessels 28, 30, 32 in the retina 20 and choroid 22 are transiently constricted prior to exposure to light radiation 46 according to the method of the invention. The retinal capillaries 28, choroidal vessels 30 and choroidal capillaries 32 are constricted in addition to vessels in the new subretinal tissue 40. Constriction of these vessels 28, 30, 32, 40 ensures that little or no photosensitizing agent 44 is contained within the vessel lumen at the site of phototreatment, thus subsequent treatment with light radiation 46, such as with a laser, will not affect the vessels 28, 30, 32, 40 themselves. This also prevents scar formation due to cumulative exposure of normal vessels 28, 30, 32 to light radiation 46. The photosensitizing agent 44, however, has accumulated in the subretinal space surrounding the neovascular tissue 40 due to leakage of photosensitizing agent 44 through fenestrations 34 in the vessel wall 42. Subsequent light treatment 46 targets only the photosensitizing agent 44 located in the area surrounding neovascular tissue 40, and thus destroys tissue in that area only, leaving normal blood vessels substantially unaffected.

This protective effect is particularly important when repeated treatments are required. For example, neovascular tissue 40 is regenerated in macular degeneration and thus requires repeated treatments to prevent the recurrence of pathology. Use of a photosensitizing agent with numerous treatments by light radiation previously resulted in cumulative damage to normal healthy vessels, 28, 30, 32. Therefore, using the method of the invention, neovascular tissue 40 is selectively destroyed while radiation-induced damage to normal tissues and vessels 28, 30, 32 is minimized or prevented.

In one embodiment of the invention, PDT is administered to an individual requiring treatment in conjunction with methods to facilitate vessel occlusion by enhancing the formation or duration of thrombi at or near the treatment site. Such methods include either physical or chemical methods to induce vasoconstriction, administration of clot-promoting agents and administration of agents that limit or prevent clot dissolution.

Agents to promote the formation of thrombi or clots in the area to be treated by PDT may enhance PDT in selective blood vessel destruction. For example, adenosine diphosphate (ADP) is known to initiate platelet aggregation. ADP may be administered into a vessel at a dose in the range from about 50 µg/kg to 10 mg/kg. ADP may be administered either prior to, during or after PDT to promote thrombi in a region undergoing treatment.

Conversely, agents to prevent dissolution of existing thrombi or clots in the area to be treated by PDT also may enhance PDT. These agents include ε-aminocaproic acid (Amicar) administered intravenously or orally at a dose of up to 8 mg/kg and preferably 4–6 mg/kg, and tranexamic acid (4-(aminomethyl)cyclohexane carboxylic acid) administered intravenously at a dose of about 25 mg/kg, and the protease inhibitor aprotinin.

Constriction of blood vessels to limit blood flow in an area to be treated by PDT may also enhance PDT. Vasoconstriction may be achieved by either physical or chemical methods. Physical vasoconstriction, as in the inflation of a blood pressure cuff or in the application of the device of the present invention, can transiently collapse a vessel to enhance PDT. This type of physical intervention to spare an internal area or lining of a tissue during a treatment while subjecting a surrounding area to treatment is analogous to the insertion of a balloon catheter through the urethra in treatment of prostate cancer or hypertrophy prior to PDT to protect the internal regions of the prostate while selectively targeting an area for PDT. Chemical methods to induce vasoconstriction can be achieved by administration of a drug such as epinephrine at a dose of up to about 8 mg/kg to limit blood flow to the area under treatment and thus enhance PDT. Vasoconstriction and/or clot promoting factors, either through enhanced clot formation or prevention of clot dissolution, are preferably administered after PDT but may be administered either before PDT, during PDT or after PDT.

Timing of the transient constriction in vessels must be monitored. Since these vessels normally supply blood to and hence nourish intraocular tissues, any constriction deprives these tissue of oxygen and other nutrients carried by the blood. Thus the time of constriction must be determined and monitored; constriction must be of a duration long enough to allow for phototreatment, but yet must be of a duration short enough to not cause irreversible tissue damage by oxygen or nutrient deprivation.

Vessel constriction can be achieved by either physical or chemical means. Physical means include external application of increasing intraocular pressure, for example, by pressing directly on a surface of the eye or by pressing on a contact lens in the eye. Pressure is increased in the range of about 40–70 mm Hg to transiently constrict or collapse the vessels 28, 30, 32, 40. Preferably, the pressure increase occurs in about five minutes or less so that the normal retinal and choroidal blood supply is not pathologically compromised for an extended period. Chemical means include administration of vasoconstrictive drugs, including but not limited to vasopressin and epinephrine.

Figure 4:
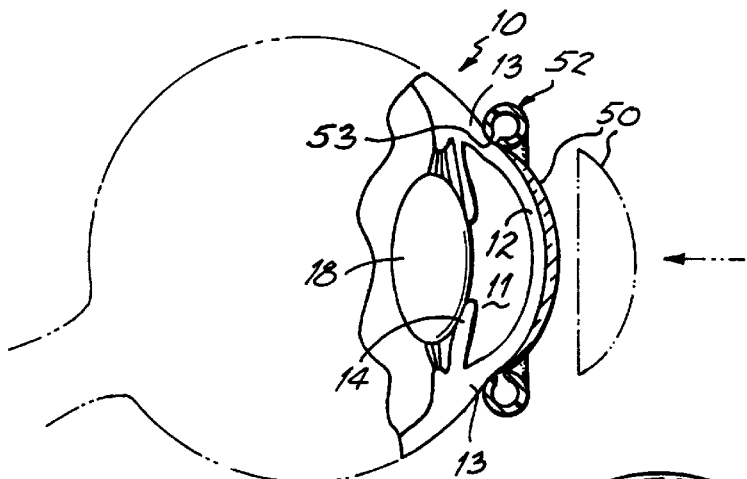
FIG. 4 is a schematic cross sectional view of a mammalian eye treated with one embodiment of the invention.
Figure 5:
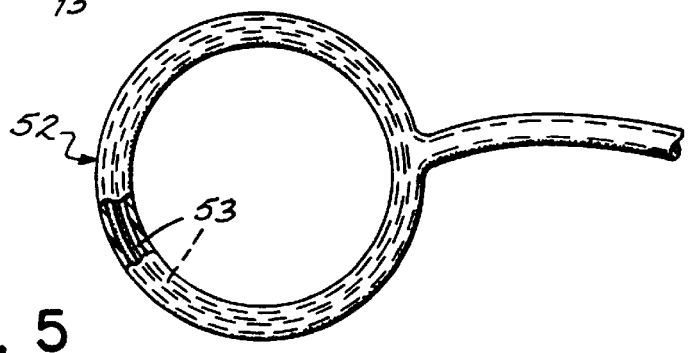
FIG. 5 is a top view of the apparatus of the invention.
Figure 6:
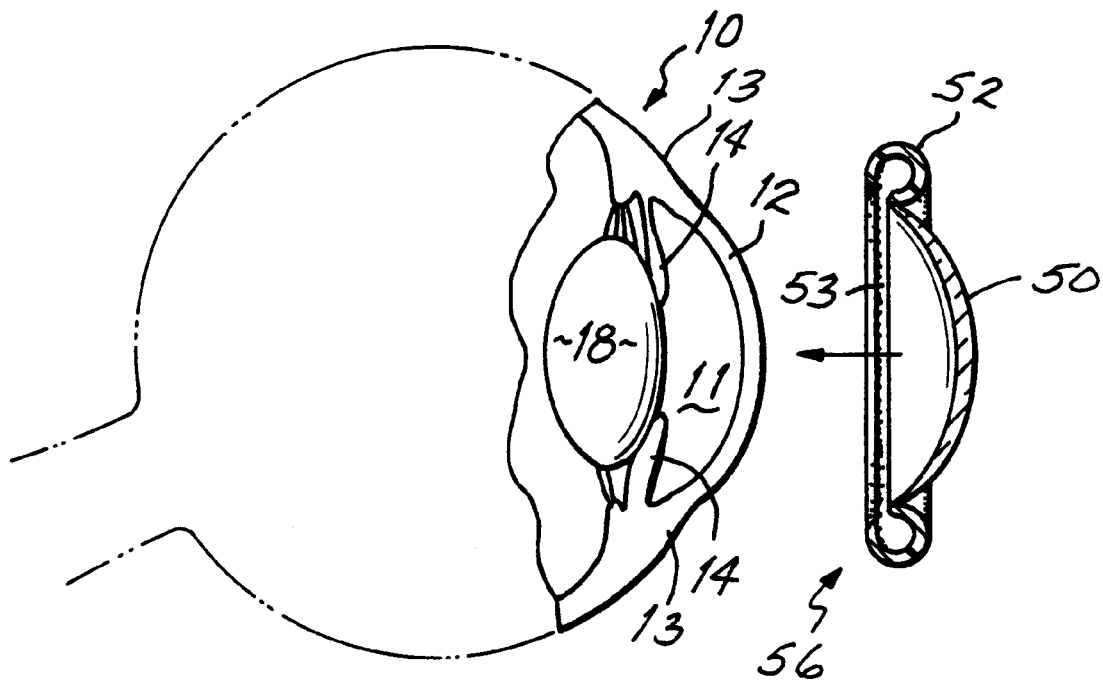
FIG. 6 is a schematic cross sectional view of a mammalian eye treated with an alternate embodiment of the invention.

With reference to FIG. 4, the intraocular pressure may be regulated by a device, comprising a contact lens 50 configured with an inflatable tube 52 applied to the cornea 12. The contact lens 50 neutralizes the refractive power of the cornea 1 2 and allows visualization of the back of the eye 10. The inflatable tube 52 has one or more perforations or holes 53 on the side of the tube 52 that is adjacent to the eye 10. This permits suction, when applied, to be transmitted to the eye 10.

The total thickness of the tube 52 is preferably about 1–5 mm, but other thicknesses may be used. The tube 52 may be made of any material that is able to withstand a vacuum sufficient to maintain an intraocular pressure of about 40–70 mm Hg without collapsing. For example, it may be made of, but is not limited to, plastic, silicone or metal or combinations of these materials. The tube 52 is preferably has a substantially circular shape to conveniently surround, either completely or partially, a contact lens. Alternatively the tube 52 may have an oval or any other shape. The tube 52 may be of any size for placement in a human eye. Preferably the tube 52 is circular with a diameter of about 12–14 mm.

The contact lens 50 portion of the device is made of any material normally used in the manufacture of contact lenses, such as glass or methacrylates. It is sized to fit over the cornea 12 according to the size of the eye 10 and is inserted over the cornea 12.

In one embodiment, the contact lens 50 and inflatable tube 52 form a unitary structure 56. The contact lens 50 portion of the device 56 serves to eliminate the refractive power of the cornea 12 and to allow the practitioner to more directly visualize the back of the eye 10. The inflatable tube 52 portion of the device 56 serves to regulate intraocular pressure and is preferably connected to a vacuum source. The device 56 is positioned on the cornea 12 and intraocular pressure is raised by applying a vacuum. In another embodiment the inflatable tube 52 is separate from the contact lens 50, thereby allowing the contact lens 50 to be applied to the cornea 12 independently of the inflatable tube 52. The latter embodiment may be useful, for example, when only manual pressure application is desired or in cases where a vacuum source is unavailable.

The tube 52 is positioned behind the cornea 12 and adjacent the sclera 16. The tube 52 is connected to a vacuum source (not shown). Suction applied to the tube 52 pushes the tube 52 against the sclera 16. The sclera 16 then indents inwardly and thus increases intraocular pressure. The inflatable tube 52 allows application, maintenance and release of pressure to the eye 10.

In use, a photosensitizer 44, preferably tin ethyl etiopurpurin (SnET2), is administered, preferably by the intravenous route, to a patient to be treated. The dose of SnET2 is about 1–2 mg/kg when given by intravenous injection. After a variable period of time to allow the photosensitizer 44 to distribute in the body and to be released into subretinal tissue, usually between about 5 min to about 30 min, the ocular vessels are transiently constricted. This is accomplished by increasing the pressure in the eye 10 using the device of the invention. The increase in pressure is preferably obtained over a period of about 5 min or less, since a longer period of time may damage the retina 20.

The patient, having been treated with a topical anesthetic such as lidocaine or Optaine (Alcon Laboratory) applied to the eye 10, has the device applied. The tube 52 is placed behind the cornea 12 and is attached to sclera 16. Pressure is applied by connection of the inflatable tube 52 to the vacuum source (not shown). An applanation tohometer may be used to measure pressure applied, which may be in range of about 5 mm Hg to greater than 500 mm Hg. Pressure may also be applied by manual compression of the inflatable tube 52 or contact lens 50. In either case, an intraocular pressure in the range of about 40–70 mm Hg is needed so that the majority of intraocular vessels are collapsed. The choroidal vessels will collapse first, then retinal vessels. During the increase in pressure the surgeon or other practitioner can observe the central retinal artery either pulsate or collapse and the retinal blood circulation to transiently cease.

After sufficient pressure has been applied to constrict or collapse the vessels 28, 30, 32, 40, PDT is immediately initiated. Light radiation 46, preferably in the form of a laser, is applied. The laser may be used at a power of about 150 mW and total energy of 50 J. Exposure of the light radiation 46 is preferentially restricted to only the area to be treated, for example by use of a laser to direct only a narrow beam of light to the area. This avoids or decreases damage to normal vessels and tissues.

Photosensitized tissues are irradiated with light at a wavelength corresponding to the absorbance spectrum of the particular photosensitizing agent. The optimal wavelength for phototreatment is selected on the basis of the appropriate action spectrum of the photosensitizing agent. For example, when ALA is administered, the resulting protoporphyrin may have an absorbance band the area around 630 nm, or alternatively, in the area of around 670 nm to encompass protoporphyrin isomers. The radiation wavelength is in the range of about 665 nm when either SnET2 or NPe6 is administered, 689 nm when benzoporphyrin derivative monoacid tube A (BPD-MA) is administered, and 732 nm when progesterone (Lutex) is administered.

After irradiation, the intraocular pressure is gradually decreased and intraocular pressure is allowed to return to normal levels. With manual pressure application, such as pressing with a finger or a hand held instrument, the pressure is gradually reduced until the finger or other source is removed from the surface of the contact lens 50. With a vacuum source of pressure, the vacuum applied to the inflatable tube 52 is gradually decreased. Gradual decrease in pressure permits the vessels 28, 30, 32, 40 to gradually resume their normal configuration. A more rapid decrease in pressure can result in retinal bleeding due to rupture of retinal capillaries.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method to selectively phototreat an abnormal intraocular blood vessel having an altered membrane without adversely affecting normal intraocular blood vessels comprising administering a photosensitizing agent susceptible to phototreatment into said normal and abnormal vessels, allowing a sufficient time for said agent to be released from said abnormal vessel through said altered membrane and into a site adjacent said abnormal vessel and maintaining said agent in said normal vessels, thereafter transiently constricting said normal vessels at a phototreatment site for displacing said agent from said normal vessels at said site and preserving said normal vessels during phototreatment, phototreating said site for a defined time during constriction of said normal vessels to selectively treat said abnormal vessel having said agent in said adjacent tissue, and thereafter restoring said normal vessels to an unconstricted state.

2. The method of claim 1 wherein said agent is administered by intravenous injection.

3. The method of claim 1 wherein said normal vessels are transiently constricted by a method selected from the group consisting of a physical constriction, a chemical constriction and combinations thereof.

4. The method of claim 3 wherein said physical constriction is by regulating pressure to said vessels.

5. The method of claim 4 wherein said pressure is increased in the range of about 40–70 mm Hg to collapse said vessel.

6. The method of claim 4 wherein said pressure is regulated by a pressure applied directly to a surface of the eye.

7. The method of claim 4 wherein said pressure is regulated by a pressure applied through an intraocular device comprising a contact lens.

8. The method of claim 7 wherein said device is an inflatable tube encircling a least a portion of said contact lens, said tube being operably attached to a vacuum source.

9. The method of claim 1 wherein said photosensitizing agent is selected from the group consisting of tin ethyl etiopurpurin, protoporphyrin, aminolevulinic acid benzoporphyrin derivative monoacid tube A, mono-l-aspartyl chlorine 6, progesterone and combinations thereof.

10. The method of claim 1 wherein said time for said agent to be released into said adjacent site is in the range of about 1 min to about 60 min post-administration of said agent.

11. The method of claim 1 wherein said time for said transient vessel constriction is less than about five minutes.

12. The method of claim 3 wherein said chemical constriction is by administration of a vasoconstrictive drug.

13. The method of claim 1 further comprising administering a vessel occluding agent selected from the group consisting of an agent to enhance thrombus formation, an agent to retard thrombus dissolution and combinations thereof.

14. The method of claim 13 wherein said agent to enhance thrombus formation is adenosine diphosphate (ADP).

15. The method of claim 14 wherein said ADP is administered at a dose of about 50 µg/kg to about 10 mg/kg.

16. The method of claim 13 wherein said agent to retard thrombus dissolution is selected from the group consisting of ε-aminocaproic acid, tranexamic acid and aprotinin.

17. The method of claim 16 wherein said ε-aminocaproic acid is administered at a dose of up to about 8 mg/kg and said tranexamic acid is administered at a dose of about 25 mg/kg.

18. The method of claim 13 wherein said agent is administered prior to, during or subsequent to PDT.

* * * * *